US00PP12997P2

(12) United States Plant Patent
Patra et al.

(10) Patent No.: US PP12,997 P2
(45) Date of Patent: Sep. 24, 2002

(54) 'JAL PALLAVI', WATER LOGGING TOLERANT *CYMBOPOGON WINTERIANUS*

(75) Inventors: Nirmal Kumar Patra; Sushil Kumar; Alok Kalra; Harikesh Bahadur Singh; Hemendra Pratap Singh; Nareshwar Mengi; Suman Preet Singh Khanuja; Ajit Kumar Shasany; Mahendra Pandurang Darokar; Ved Ram Singh; Hasan Tanveer; Arif Ali Naqvi; Paltoo Ram; Vijay Pal Singh; Kambod Singh; Dharmendra Kumar Rajput; Birendra Kumar; Jitendra Pal Singh; Raja Ram; Vijay Kumar; Sheo Ram Sharma, all of Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/263,790

(22) Filed: Mar. 5, 1999

(30) Foreign Application Priority Data

Feb. 12, 1999 (IN) ..... 237/Del/99

(51) Int. Cl.[7] ..... A01H 5/00

(52) U.S. Cl. ..... Plt./384

(58) Field of Search ..... Plt./384

*Primary Examiner*—Bruce R. Campell
*Assistant Examiner*—Annette H. Para
(74) *Attorney, Agent, or Firm*—Birch Stewart Kolasch & Birch LLP

(57) ABSTRACT

The present invention is related to the development of a new and distinct vegetatively propagated water tolerant plant of *Cymbopogon winterianus* by selection of a somatic variant from high yielding line Jorlab-2, the selected plant withstands prolonged water stagnation with no reduction in yield of essential oil.

5 Drawing Sheets

FIELD OF INVENTION

The present invention relates to an aquatic stress tolerant high yielding citronella plant 'Jal Pallavi'. More particularly, the innovation relates to the development of an aquatic stress tolerant high yielding citronella plant through extensive clonal selection for the spontaneous genetic variants under artificial water stress conditions of sustained stagnation. These selections were made under high stringency of surviving ability and normal growth behavior under prolonged water stagnation in vegtatively multiplied large population of citronella ('Jorlab-2'). The variety being propagated vegetatively by tillers and is stable for commercial cultivation.

BACKGROUND OF THE INVENTION

Water stagnation over undulated soil surface in a large perennial plantation of citronella leads to physiological damage (plant sickness) and even significant level of plant mortality. This as a consequence reduces the total crop productivity. Until now, not even a single high yielding variety is available which would successfully withstand water stagnation and sustain its high productivity even under aquatic situation. Unlike other perennial aromatic grasses (lemongrass and Palmarosa) citronella suffers from a drawback that it does not set viable seeds. Thus, from breeding angle, the scope of improving its plant traits is absolutely confined to genetic manipulations at clonal level. Keeping this limitation of the plant in view, planned efforts were made at this Institute's (CIMAP's) headquarters at Lucknow and its field station Pantnagar to explore the possibility of obtaining a water tolerant genotype with high yield potential within the otherwise high yielding variety through its extensive clonal selections.

SUMMARY OF THE INVENTION

To overcome the above difficulties, the present invention provides a novel, distinct, high yielding and stable variety of citronella plant *Cybopogon winterianus,* named as 'Jal Pallavi' characterived by the following combination of characteristics:

(a) a variant (mutant) of the normal citronella variety 'Jorlab-2' with distinct morphology that was selected and isolated through large scale screening for any spontaneous arising variability, (b) highly adapted to both favorable as well as unfavorable environments of continuous and aberrant water stagnation situations, (c) production of more biomass (herbage yield) in comparison to the existing citronella varieties, (d) production of essential oil with pleasant smell conforming to the standard concentrations for the major oil components citronellal, citronellol and geraniol much useful in pharmaceutical/aromatic preparations for various applications, (e) unique RAPD profile, compared to those of the existing citronella varieties, (f) exhibiting least reduction in yield (hergabe as well as essential oil) over years and thus constitutes the most suitable material for perennial plantations, and (g) substantially high oil yield, at least 1.22%, with the following oil constituents to a maximum extent of citronellal at least 40.7%, citronellol at least 10.7% geraniol at least 17.5% and the rest being unidentified fractions in the essential oil, all totaling to 100% at different stages of growth, substantially as shown and described.

DETAILED DESCRIPTION

Breeding History

Figure 1:
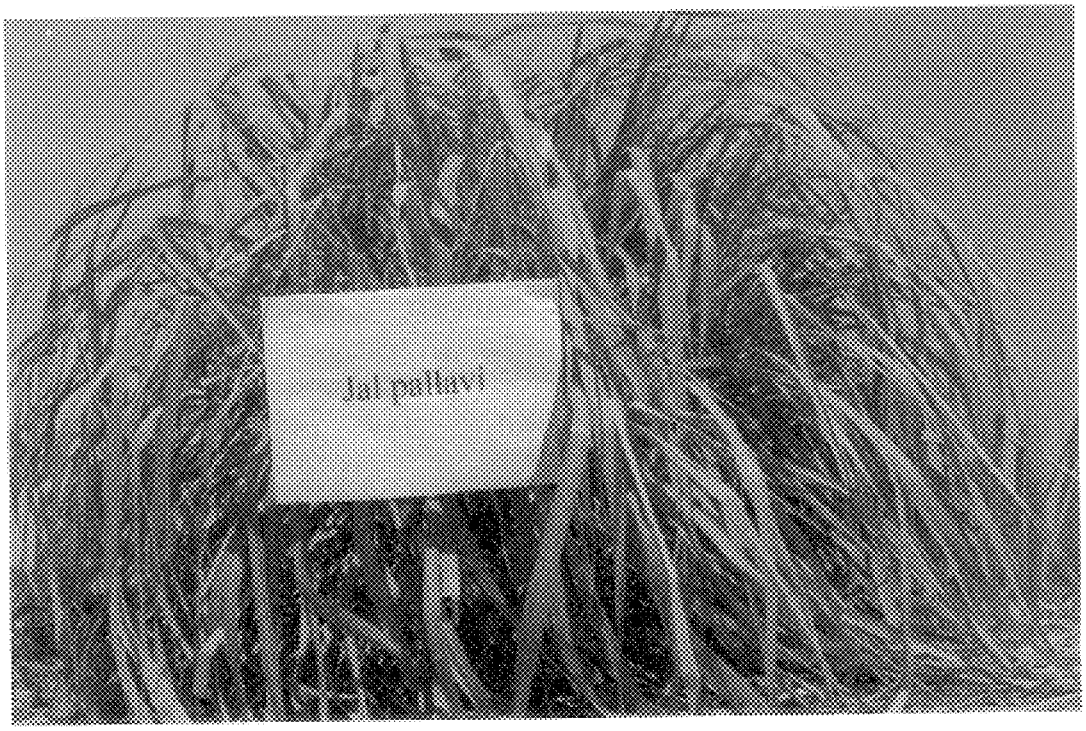
FIG. 1. A 3 year old plant of Jal Pallavi.

'Jal Pallavi' is an out-come of a strategic approach of vegetatively multiplying a specific variety of citronella to develop a large clonal population to serve as a pool for selections of a water logging tolerant genotype. It has been grown and developed at Field station at Pantnagar, Uttar Pradesh, India. The institute where the inventors reside and do research is called "Central institute of Medicinal & Aromatic Plants" and is situated at Lucknow. The place where field trials had been carried is a field station called "Pantnagar". This is a small place near the city of Lucknow. Lucknow and Pantnagar are both in the State of Uttar Pradesh in India.

The water tolerant plant namely 'Jal Pallavi' of this invention is an out-come of a strategic approach of vegetatively multiplying a specific variety of citronella to develop a large clonal population to serve as a pool for selections. The objective of the selection was to identify and isolate a spontaneous genetic variant possessing significant water tolerance ability coupled with high oil yield under artificially created situation of water stagnation. Among the existing citronella (Java citronella type of the trade) varieties in India, 'Jorlab-2' is one of the popular varieties but is susceptible to water stagnation in the farmers fields. This variety was identified as the starting genetic material for exercising the clonal selections. We planted a large population in the field comprising 5000 slips having intact root regenerating base of the mother variety 'Jorlab2'.

Immediately after their planting, the slips at the tiller pre-emergence phase were exposed to artificially created aquatic situations as shown in Photograph # 1 with 8 cm water stagnation (referred as "treatments" for sake of brevity in the discussion) keeping each water-treatment sustained for one month and allowing 7 days dry interval between two treatments. The distinct effect of such prolonged water treatment could be recorded after 15 days of planting and there of, 15 days of water exposure. From the huge population of 5000 clones, only one plant revealed the unusual potential for withstanding the prolonged water stagnation and even sustaining much normal growth behavior under water stagnation showing the rarity of the desirable genetic change. Rest of the plants, despite their ostensible survival against water stagnation, were observed to be greatly impeded of the root development and tiller initiation phase. These plants with rare exception of showing 1–2 tillers as shown in Photograph # 2 having poor root growth, did not exhibit normal vegetative reproducibility throughout the whole experimental period of one year (1994–95) apart from remaining as late rooted weak plants (mostly mono-stemmed). The variant plant with normal growth habit under the aquatic situation was thus identified and isolated as shown in Photograph # 3 and was first labeled as WTC-1 (Water Tolerant Citronella) and later christened as 'Jal Pallavi' (Jal=water; Pallavi=endowed with many leaves) to distinguish it from the rest physiologically weak 'Jorlab-2' plants under water stress condition. 'Jal Pallavi' was vegetatively multiplied at a large scale following the confirmation of its reproducible property of tolerating water stagnation. It was subsequently assessed in normal fields for its productivity against its parent variety 'Jorlab-2' as well as the other high yielding varieties of citronella namely, 'Manjusha', 'Mandakini' and 'Bio-13' (earlier released by CIMAP for cultivation). Comparative appraisal of morpho-physiological fitness and productivity of cultivar 'Jal Pallavi' against the parent variety and the said other varieties was carried out through a preliminary yield trial during 1995–96 under normal field conditions (Table 1).

TABLE 1

Comparative growth performances of 'Jal Pallavi' and other varieties of citronella in a yield trial (1995–96) conducted under normal field conditions at Pantnagar.

| Variety/ Strain | Plant height (cm) | Number of tillers per plant | Leaf length (cm) | Leaf width (cm) | Herbage yield per plant (g) | Oil content (%) |
|---|---|---|---|---|---|---|
| Bio-13 | 78.7 | 81 | 67.6 | 1.6 | 600.0 | 1.12 |
| Manjusha | 82.6 | 86 | 70.0 | 1.7 | 703.3 | 0.95 |
| Mandakini | 78.5 | 78 | 67.3 | 1.8 | 602.7 | 0.87 |
| Jorlab-2 | 76.3 | 72 | 65.3 | 1.5 | 553.3 | 0.77 |
| Pantnagar local | 79.6 | 69 | 58.7 | 1.4 | 490.0 | 0.93 |
| Jal Pallavi | 95.7 | 94 | 72.0 | 1.5 | 893.3 | 1.22 |
| CD (5%) | 5.4 | 5.3 | 4.4 | 0.2 | 175.0 | |

As evident the selected plant 'Jal Pallavi' demonstrated the supremacy over all the varieties for yield attributes as well as plant growth. It showed a significant increase of plant height by 13.1 cm over the tallest variety 'Manjusha' and 19.4 cm over the parent 'Jorlab-2'. Increase in tillering was 10% over 'Manjusha' and 30% over parent 'Jorlab-2'. The increase in herbage yield was 27% over the best check 'Manjusha' and 63% over parent. Oil content showed an increase of about 9% over best check 'Bio-13'. 28% over 'Manjusha' and 71% over 'Jorlab-2'. This significant improvement prompted us to conduct Pilot Scale Trials (PST) over three years (1996–97, 1997–98 and 1998–99).

A unique morphological feature that enables Jal Pallavi to be distinct from the existing normal varieties is that it quickly elongates its stems (culms) lying between the plant base and leaf sheaths under both normal and waterlogging situation. Its elongated stem part being very hard and rigid with large number of compact nodes (8–12 against 4–5 of the normal plants) and short internodes (1.5 to 2.0 cm against 2.0 to 3.0 cm of the normal varieties) and having no leaves, Jal Pallavi is quite capable of placing the base of leaf sheaths with leaf meristems above the level of stagnant water. Indeed, this very unique feature of stem elongation at the basal part of the plant can be considered as the major 'morphological marker' for water logging tolerance of the new variety Jal Pallavi (Sheet #3, Photograph 190 4, Jal Pallavi with the distinct stem elongation shown at the right side).

TABLE 2

Comparative performance of 'Jal Pallavi' and other varieties of citronella for herbage yield in PST at Pantnagar, under normal field conditions (Plot Size: 16 m × 5 m).

| | 1996–97 Plot yield (kg) in the harvest no. | | | | 1997–98 Plot yield (kg) in the harvest no. | | | |
|---|---|---|---|---|---|---|---|---|
| Variety/Strain | 1 | 2 | 3 | Total | 1 | 2 | 3 | Total |
| Bio-13 | 46.0 | 81.6 | 80.7 | 208.3 | 45.6 | 78.0 | 59.5 | 183.1 |
| Manjusha | 53.3 | 89.8 | 115.4 | 258.5 | 52.5 | 85.5 | 94.8 | 232.8 |
| Mandakini | 60.8 | 93.4 | 103.4 | 257.6 | 56.7 | 84.8 | 83.2 | 224.7 |
| Jorlab-2 | 58.5 | 102.7 | 97.7 | 259.0 | 56.0 | 101.3 | 68.0 | 225.3 |
| Pantnagar Local | 40.5 | 81.1 | 66.4 | 188.0 | 39.8 | 78.5 | 55.3 | 173.6 |
| Jal Pallavi | 68.6 | 114.4 | 92.2 | 275.2 | 65.1 | 110.5 | 90.3 | 266.0 |
| CD (5"/0) | | | | 37.2 | | | | 32.2 |

| | 1998–99 Plot yield (kg) in the harvest no. | | | | Herbage yield Per plot/ year | Herbage yield Per ha/ year |
|---|---|---|---|---|---|---|
| Variety/Strain | 1 | 2 | 3 | Total | (kg) | (q) |
| Bio-13 | 40.7 | 72.4 | 51.5 | 164.6 | 185.3 | 231.6 |
| | | | | | | 43.4 |
| Manjusha | 47.3 | 82.6 | 66.8 | 196.7 | 229.3 | 286.6 |
| | | | | | | 16.0 |
| Mandakini | 51.7 | 85.4 | 69.2 | 206.3 | 229.5 | 296.8 |
| | | | | | | 15.8 |
| Jorlab-2 | 50.8 | 81.1 | 59.0 | 191.0 | 225.1 | 181.1 |
| | | | | | | 18.1 |
| Pantnagar Local | 37.5 | 73.5 | 40.3 | 151.3 | 171.0 | 213.6 |
| | | | | | | 55.5 |
| Jal Pallavi | 63.0 | 106.5 | 86.7 | 256.2 | 265.8 | 332.1 |
| CD (5"/0) | | | | 25.2 | 27.0 | |

*Percent improvement for herbage yield in 'Jal Pallavi' over the other varieties is shown by values that are underlined.

TABLE 3

Comparative performance of 'Jal Pallavi' and the other varieties of citronella for oil yield in PST at Pantnagar, under normal field conditions (Plot Size: 16 m × 5 m)

| | 1996–97 Plot yield (kg) in harvest no. | | | | 1997–98 Plot yield (kg) in harvest no. | | | |
|---|---|---|---|---|---|---|---|---|
| Variety/strain | 1 | 2 | 3 | Total | 1 | 2 | 3 | Total |
| Bio-13 | 0.61 | 0.57 | 1.03 | 2.21 | 0.61 | 0.55 | 0.77 | 1.93 |
| Manjusha | 0.64 | 0.60 | 1.15 | 2.40 | 0.62 | 0.56 | 0.94 | 2.12 |
| Mandakini | 0.59 | 0.56 | 1.03 | 2.20 | 0.56 | 0.53 | 0.82 | 1.91 |
| Jorlab-2 | 0.55 | 0.51 | 0.82 | 1.88 | 0.63 | 0.52 | 0.57 | 1.62 |
| Pantnagar Local | 0.53 | 0.47 | 0.80 | 1.80 | 0.51 | 0.46 | 0.65 | 1.62 |
| Jal Pallavi | 1.0 | 0.91 | 1.27 | 3.18 | 0.93 | 0.89 | 1.26 | 3.08 |
| CD (5%) | | | | 0.36 | | | | 0.22 |

| | 1998–99 Plot yield (kg) in harvest no. | | | | Oil yield per plot/ year | Oil yield per ha/ year |
|---|---|---|---|---|---|---|
| Variety/Strain | 1 | 2 | 3 | Total | (kg) | (q) |
| Bio-13 | 0.54 | 0.51 | 0.67 | 1.72 | 1.95 | 243.7 |
| | | | | | | 58.0 |
| Manjusha | 0.62 | 0.54 | 0.68 | 1.84 | 2.12 | 265.0 |
| | | | | | | 45.3 |

TABLE 3-continued

Comparative performance of 'Jal Pallavi' and the other varieties of citronella for oil yield in PST at Pantnagar, under normal field conditions (Plot Size: 16 m × 5 m)

| | | | | | | |
|---|---|---|---|---|---|---|
| Mandakini | 0.52 | 0.51 | 0.70 | 1.73 | 1.94 | 242.5 |
| | | | | | | 58.8 |
| Jorlab-2 | 0.47 | 0.40 | 0.50 | 1.37 | 1.62 | 202.5 |
| | | | | | | 90.1 |
| Pantnagar Local | 0.47 | 0.44 | 0.48 | 1.40 | 1.60 | 200.0 |
| | | | | | | 92.5 |
| Jal Pallavi | 0.92 | 0.85 | 1.21 | 2.98 | 3.08 | 385.0 |
| CD (5%) | | | | 0.16 | 0.25 | 31.25 |

*Percent improvement for oil yield in 'Jal Pallavi' over the other varieties is shown by values that are underlined.

Pilot Scale Yield Trials (PST) were conducted in a Randomized Block Design (RBD) fashion with three replications for each treatment. In each trial, the plants were grown with 45 cm×30 cm plant-spacing in each plot of 16 m×5 m size and were maintained for 4 years (1995–99) by providing the normal cultural practices and fertilizer dosage at 150:80:60 ($N_2$:$P_2O_5$:$K_2O$) each year. The data on green herbage and oil productivity in the varieties were collected consecutively for 3 years (1996–99) availing three harvests (cuts) per year, the harvesting schedule being: April, August and November for each year. The yearly averages for per hectare herbage (Table 2) and oil yield (Table 3) in 'Jal Pallavi' were: 332.1 q and 385.0 kg, rewpectively as against corresponding figures: 231.6 q and 243.7 kg in 'Bio-13', 286.6 q and 265.0 kg in 'Manjusha', 286.9 q and 242.5 kg in 'Mandakini', 281.1 q and 202.5 kg in 'Jorlab-2' (mother variety) and 231.6 q and 200 kg in 'Pantnagar Local'. Analysis of these results for average productivity of the varieties vis-a-vis their productivity trends over the three years (1996–99) evidently demonstrated that 'Jal Pallavi' besides exhibiting mazimum per hectare per year average yield, shows the least reduction over the years which amounted to negligible proportions (3–6% as against 10–27% in the other varieties (Table 2 & 3), a desirable feature for perennial plantations. Thus, it was apparent that 'Jal Pallavi' is the best genotype in citronella so far, in terns of both high yielding ability and stability in yield. Consistent with the results of productivity trends in the varieties were, observations on the varying degrees of plantation sickness associated with soil undulation-led water stagnation in the varieties. It is noteworthy that in all the varieties except 'Jal Pallavi', the occurrence of physiologically weak plants invariably associated with the depressed soil patches having stagnant water is very common, especially in the third year after planting. Such sick plants are conspicuously damaged with hardly 1–5 surviving tillers as against the healthy plants of 'Jal Pallavi', each having 55–88 tillers under the same condition.

The performance of 'Jal Pallavi' in the PST under water logged situation created by stagnating 8 cm water in a sustained manner very clearly demonstrated its substantial superiority against all other varieties and checks (Table 4). While all other varieties showed poor tillering, herbage and oil yield under these conditions, 'Jal Pallavi' behaved quite parallel to its potential under normal conditions. As evident the advantage in case of 'Jal Pallavi' was of 4.96 folds for herbage yield and 6.36 folds for oil yield over the checks.

TABLE 4

Comparative performances of 'Jal Pallavi' and other varieties of citronella for tiller number and herbage and oil yield under 8 cm water logged situation in PST at Pantnagar (Plot size: 16 m × 5 m; plot yield pooled over three seasons in each year)

| | 1997–1998 | | | | | |
|---|---|---|---|---|---|---|
| | Tiller no./ per Plant | | Herbage yield per | | Oil yield per | |
| | | | plot 11 | ha | plot | ha |
| Variety/Strain | IC | FC | (kg) | (kg) | (kg) | (q) |
| Bio-13 | 16 | 18 | 54.5 | 68.1 | 0.50 | 62.5 |
| Manjusha | 20 | 23 | 66.7 | 83.4 | 0.60 | 75.0 |
| Mandakini | 18 | 20 | 58.2 | 72.8 | 0.50 | 62.5 |
| Jorlab-2 | 12 | 14 | 40.0 | 50.0 | 0.30 | 37.5 |
| Pantnagar Local | 15 | 17 | 49.6 | 62.0 | 0.40 | 50.0 |
| Jal Pallavi | 28 | 82 | 230.6 | 288.5 | 2.54 | 317.5 |
| CD (5%) | — | 8.5 | 78.3 | — | 0.75 | — |

| | 1998–1999 | | | | | | | |
|---|---|---|---|---|---|---|---|---|
| | Tiller no. | | Herbage yield per | | Oil yield per | | Yield of | |
| | | | | | | | herbage/ | oil/ha |
| Variety/ | plant | | plot | ha | plot | ha | ha/year | year |
| Strain | IC | FC | (kg) | (q) | (kg) | (q) | (q) | (kg) |
| Bio-13 | 15 | 13 | 44.3 | 51.6 | 0.40 | 50.0 | 60.0 | 56.2 |
| Manjusha | 18 | 15 | 45.3 | 56.3 | 0.40 | 50.0 | 70.0 | 62.5 |
| Mandakini | 17 | 14 | 42.7 | 54.6 | 0.36 | 45.0 | 63.7 | 53.8 |
| Jorlab-2 | 10 | 8 | 25.5 | 32.0 | 0.20 | 25.0 | 41.0 | 31.2 |
| Pantnagar Local | 12 | 10 | 35.6 | 44.5 | 0.30 | 37.5 | 53.2 | 43.8 |
| Jal Pallavi | 78 | 76 | 226.7 | 283.4 | 2.50 | 312.5 | 286.0 | 315.0 |
| CD (5%) | — | 7.2 | 73.8 | — | 0.68 | — | — | — |

IC: Initial count of tillers at the time of 8 cm water stagnation treatment in field.
FC: Final count of tillers after one year's treatment.

Objective Description of the Variety a) Genus: Cymbopogon.
b) Species: *Winterianus*.
c) Family: Gramineae.
d) Common name: Citronella (Java citronella of trade)
e) Plant height: 95.7±1.2 cm against, 76.3±1.1 cm, 82.6±1.3 cm of 'Jorlab-2', 'Bio-13' and 'Manjusha', respectively (Table 1).
f) Growth habit: Highly synchronous growth habit with long tillers.
g) Stem (culm): Moderately bold.
h) Leaf: Moderately-broad and thick and light green (146B). (Table 1).
i) Inflorescence: Racemose spike.
j) Active constituents: Citronellal 40.7%, Citronellol 10.7% and Geraniol 17.5% as against the corresponding values for these constituents: 36.9%, 10.5% and 21.9% in the mother variety 'Jorlab-2' and 44.5%, 10.5% and 20.6%, in 'Bio-13'.

Culms, up to 1.5 cm diam at the base, length 24–30 cm unbranched above, with glabrescent 8–12 nodes (against 4–5 in the normal varieties), length of internode 1.5–2.0 cm (against 2.0–3.0 cm in the normal varieties).

Leaves not basally aggregated, 5–8 in number, (against rarely our 6 in the normal varieties)

Leaf blades linear, 90–110 cm long (against 68–95 cm of the other varieties) and not more than 1.5–2.0 cm wide.

Leaf surface glabrous with scabrous margins, glaucous beneath narrowed to the base; Leaf tip long acuminate; Sheaths smooth, glabrous and striate. Legules scarious and 0.3–0.4 cm long (against. 0.20–0.25 cm of the other varieties) and often lacerate. Leaf color light green 146B) (Table-1).

f) Inflorescence

Large (30–35 cm) decompound, panicle, ultimate branches strict with 2–3 peduncles, spathules from each spathe; Racemes 20 cm long, one sessile or short and the other longer pedicelled with the two lower spikelets, homogenous, male or neuter. The pedicel not swollen, the remaining pair in both racemes heterogamous. Ovary with 1 carpal, unilocular, stigma bifid, lateral and feathery, superior, ovule single, erect.

Seeds terete, 0.2 cm long, very rarely viable like that of all known varieties leading the plant to solely depend upon the vegetative (asexual) means for its propagation. Vegetative propagation solely via rooted tillers (slips), homogenous and genetically true to the mother plant (the first water tolerant variant of Jorlals-2).

The mentioned stem (clum) is an elongation at the basal part of its plants (sheet # 3, photograph #1) is a major "morphological marker" for identifying its water tolerance. The formation of nodes in high number (8–12 as against 4–5 of the normal varieties) with low internodal distance (1.5–2.0 cm against 2.0–3.0 cm) and longer culm length (24–30 cm against 5–10 cm of the normal varieties) in 'Jal Pallavi', distinctly mark it from the short-culmed normal varieties at both normal and water logging field situation.

In contrast to the prevailing belief that in aromatic plants relationship between oil quantity and oil quality is inverse, the improvement in 'Jal Pallavi' (Table 5 & Table 6) over the existing varieties, for oil productivity, has not been accompanied by reduction in oil quality. This was revealed by the results of the quality analysis of essential oil samples, prepared from 'Jal Pallavi' and its mother variety 'Jorlab-2' and then were examined by Gas Liquid Chromatography (GLC). With the percent concentration of the major essential oil constituents: citronellal, citronellol and geraniol being 40.7, 10.7 and 17.5, in the quality of 'Jal Pallavi' essential oil could be considered quite consistent with that of the mother variety having corresponding values 36.9, 10.5 and 21.9 (The total area under the three peaks against these three major constituents in the two genotypes measures 68.9 and 69.3, respectively).

The color codes are according to the R.H.S. color chart published by The Royal Horticultural Society, 80 Vincent Square, London SW1P 2PE,1995. The above examples are only illustrative in nature and should not be construed to limit the scope of the invention.

TABLE 5

Oil content (%) in different Cymbopogon crop varieties (estimated by glass distillation)

| | Oil content (%) during | | |
|---|---|---|---|
| Variety/strain | Summer | Rains | Winter |
| I. Citronella | | | |
| i) Bio 13 | 1.35 | 0.70 | 1.30 |
| ii) Manjusha | 1.20 | 0.66 | 1.00 |
| iii) Mandakini | 1.00 | 0.60 | 1.00 |

TABLE 5-continued

Oil content (%) in different Cymbopogon crop varieties (estimated by glass distillation)

| Variety/strain | Oil content (%) during Summer | Rains | Winter |
|---|---|---|---|
| iv) Jorlab-2 | 0.95 | 0.50 | 0.85 |
| v) Pantnagar Local | 1.10 | 0.60 | 1.10 |
| vi) Jal Pallavi | 1.45 | 0.80 | 1.40 |
| II. Palmarosa | | | |
| 0 PRC-1 | 0.70 | 0.50 | 0.65 |
| III. Lemongrass | | | |
| i) GRL-1 | 0.60 | 0.40 | 0.60 |

TABLE 6

Yield of essential oil upon hydro-distillation of the herbage of 'Jal Pallavi' and other varieties of citronella (same distillation tank used for all the entries) at PST (1996–97 and 1997–98, Plot Size: 25 m × 10 m and Data pooled over 3 harvests/year).

| Variety/ strain | Total area ($m^2$) harvested and distilled | Total amount of herb distilled (kg/plot) 1996–97 | 1997–98 | Total amount of oil obtained (kg/plot) 1996–97 | 1997–98 |
|---|---|---|---|---|---|
| Bio-13 | 250 | 660.8 | 560.2 | 5.3 | 4.5 |
| Manjusha | 250 | 668.5 | 568.6 | 5.5 | 4.7 |
| Mandakini | 250 | 662.0 | 552.8 | 5.3 | 4.4 |
| Jorlab-2 | 250 | 658.4 | 522.7 | 5.0 | 4.0 |
| Pantnagar Local | 250 | 602.6 | 511.0 | 4.2 | 3.6 |
| Jal Pallavi | 250 | 872.3 | 858.8 | 8.0 | 7.6 |

| Variety/strain | Estimated yield/ha/year at pilot scale for Herbage (q) | Oil (kg) | Percent improvement in 'Jal Pallavi' over the other varieties for Herb yield | Oil yield |
|---|---|---|---|---|
| Bio-13 | 244.2 | 195.6 | 41.8 | 59.5 |
| Manjusha | 251.0 | 204.0 | 38.0 | 53.0 |
| Mandakini | 243.0 | 194.0 | 42.5 | 60.8 |
| Jorlab-2 | 236.2 | 180.0 | 46.3 | 73.3 |
| Pantnagar Local | 222.7 | 156.0 | 55.4 | 100.0 |
| Jal Pallavi | 346.2 | 312.0 | — | — |

Statement of Distinction

As evident from the morphology the plant of 'Jal Pallavi' is distinct from its mother variety 'Jorlab-2' as well as the other existing varieties. The mentioned stem elongation at the basal part of its plants as shown in Photograph #4 is a major "morphological marker" for identifying its water tolerance. The plant is superior to the normal citronella varieties in respect to growth habit and physiological fitness for withstanding the hostile environments of water stagnation situation that often happens with soil undulations in old perennials, and also shows high oil content and high oil content and high oil yield. The water tolerance of the plant is a major marker for the prognosis of its high physiological fitness. The significant physiological fitness for water tolerance coupled with high yield potentials in 'Jal Pallavi' is unique and hence, can be considered as a new strain available with none but us (The Institute, CIMAP, Lucknow, India).

The genotype of the plant, though unique compared to other normal varieties, has a considerable similarity (~80%) with its mother variety 'Jorlab-2'. The DNA profiling results through RAPD analysis and the records of morpho-physiological appraisals of the plant, when considered together reveal that the plant has perhaps, derived its origin from spontaneous mutation of gene(s) in its mother variety 'Jorlab-2'.

The novelty of the invention is that 'Jal Pallavi', apart from distinguishing itself from the other varieties by having meaningful water tolerance coupled with high productivity and productivity stability, shows additional distinctiveness by possessing the following combination of morpho-genetic and physiological characters.

a. The plant has long stature in comparison to other released varieties (95.7±1.2 cm against. 76.3±1.1 cm, 78.7±1.5 cm and 82.6±1.3 cm of 'Jorlab-2', 'Bio-13' and 'Manjusha', respectively; (Table 1).

b. The plant has potentiality in simultaneously generating large number of long tillers i.e. high somatic reproducibility leading to high biomass productivity (94 tillers against 72, 81 and 86 of 'Jorlab-2', 'Bio-13' and 'Manjusha', respectively (Table 1).

c. Unlike all other normal citronella varieties, the plant can quickly elongate the stems (culms) lying between plant base and leaf sheaths by formation of very hard nodes and internodes in both aquatic and normal field situations.

d. The plant has relatively high oil content potential (1.22%) in comparison to the other varieties with 0.77–1.12% oil content in addition to being water tolerant when grown in water stagnation.

Accordingly the invention provides a novel, high yielding and stable plant of *Cymbopogon winterianus,* 'Jal Pallavi' having the following combination of characters.

a. The said plant is a variant (mutant) of the normal citronella variety 'Jorlab-2' with distinct morphology that was selected and isolated through large scale screening for any spontaneously arising variability.

b. The plant is highly adapted to both favorable as well as unfavorable environments of continuous and aberrant water stagnation situations.

c. The plant produces more biomass (herbage yield) as well as essential oil in comparison to the existing citronella varieties.

d. The plant has essential oil with pleasant smell conforming to the Standard I concentrations for the major oil components citronellal, citronellol and geraniol much useful in pharmaceutical/aromatic preparations for various applications.

e. The plant has unique RAPD profile, compared to those of the existing citronella varieties.

f. The plant slows the least reduction in yield (herbage as well as essential oil) over years and thus constitutes the most suitable material for perennial plantations.

In another embodiment the novel plant shows substantially high oil yield of at least 1.22% with the following oil constituents to a maximum extent of citronellal (at least 40.7%), citronellol (at least 10.7%), geraniol (at least 17.5%) and the rest being unidentified fractions in the essential oil all totaling to 100% at different stages of growth.

Botanical Details

Figure 2:
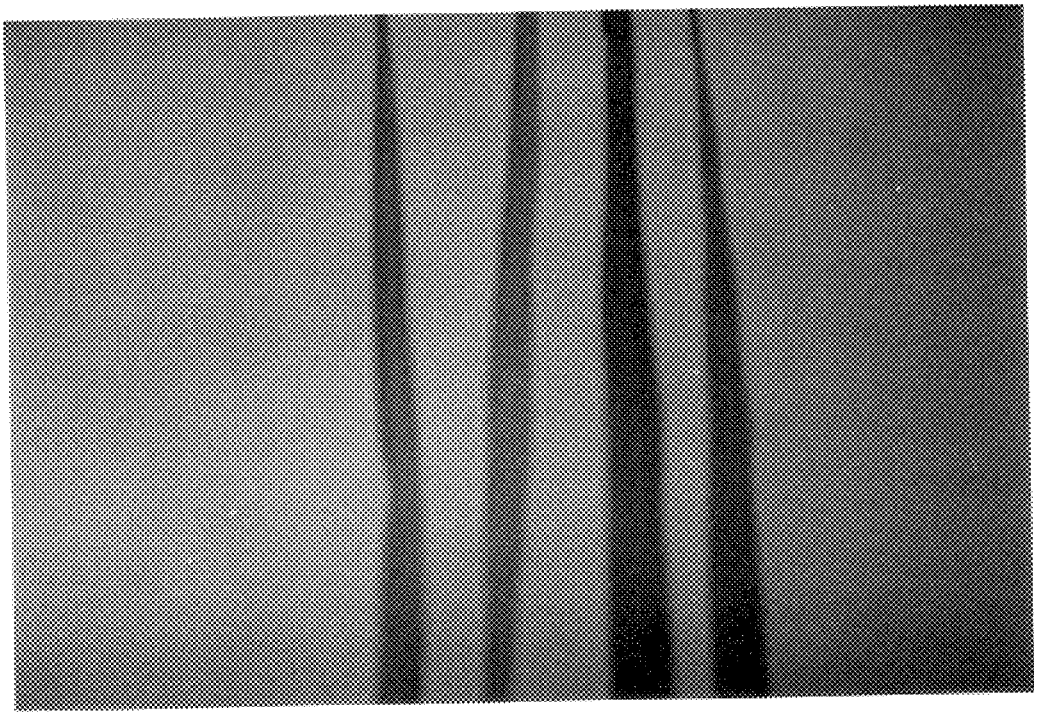
FIG. 2. Two yellow green leaves (colour code '246B' on R.H.S. colour chart of 'Jal Pallavi' (Right) compared to the two deep green leaves (colour code '146A' on R.H.S. colour chart of normal variety (Left).
Figure 3:
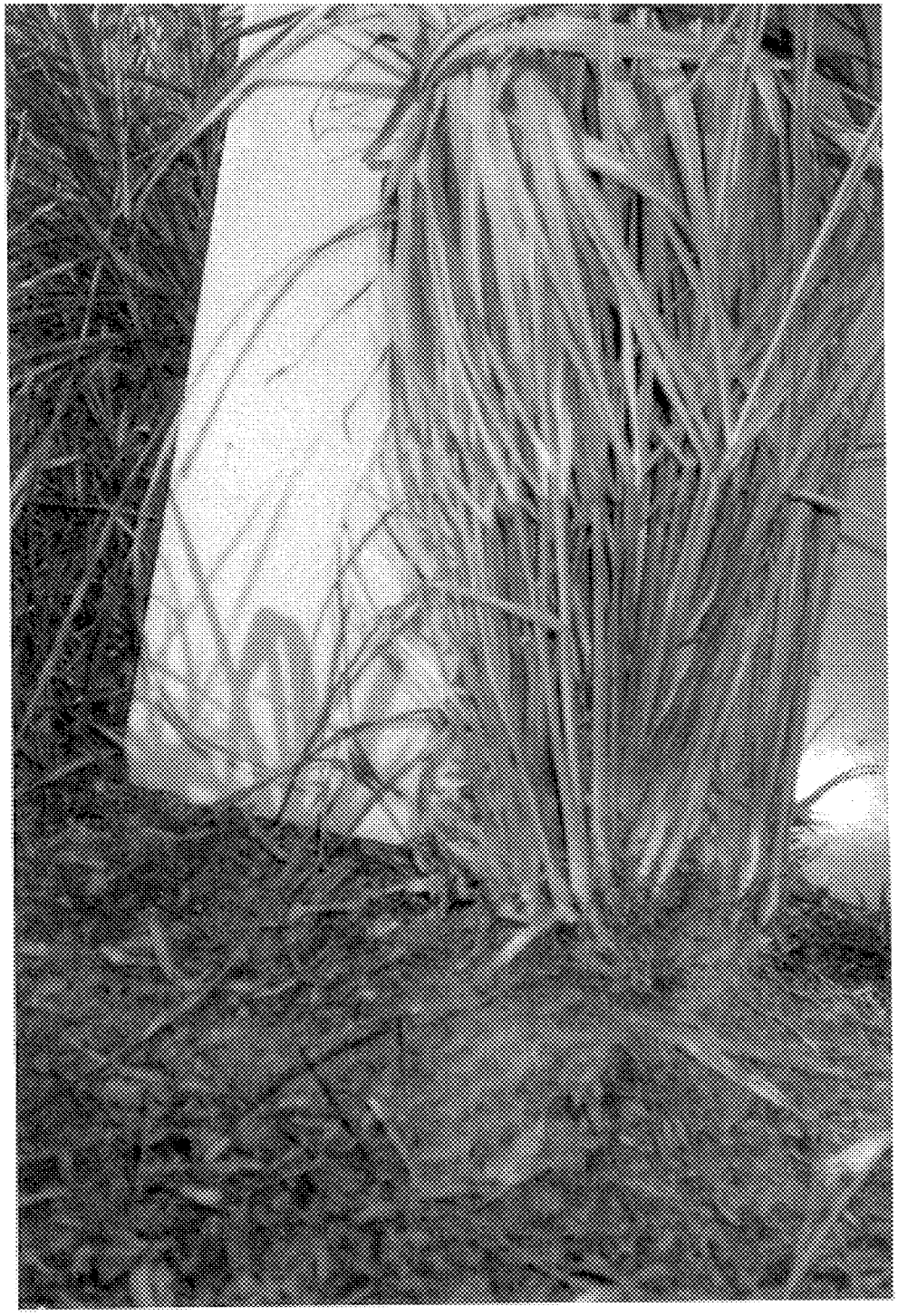
FIG. 3. A 'Jal Pallavi' plant (2 years old) showing yellow green leaves (colour code '146B' on R.H.S. colour chart) and red purple leaf sheath (colour code '70B' on R.H.S. colour chart).
Figure 4:
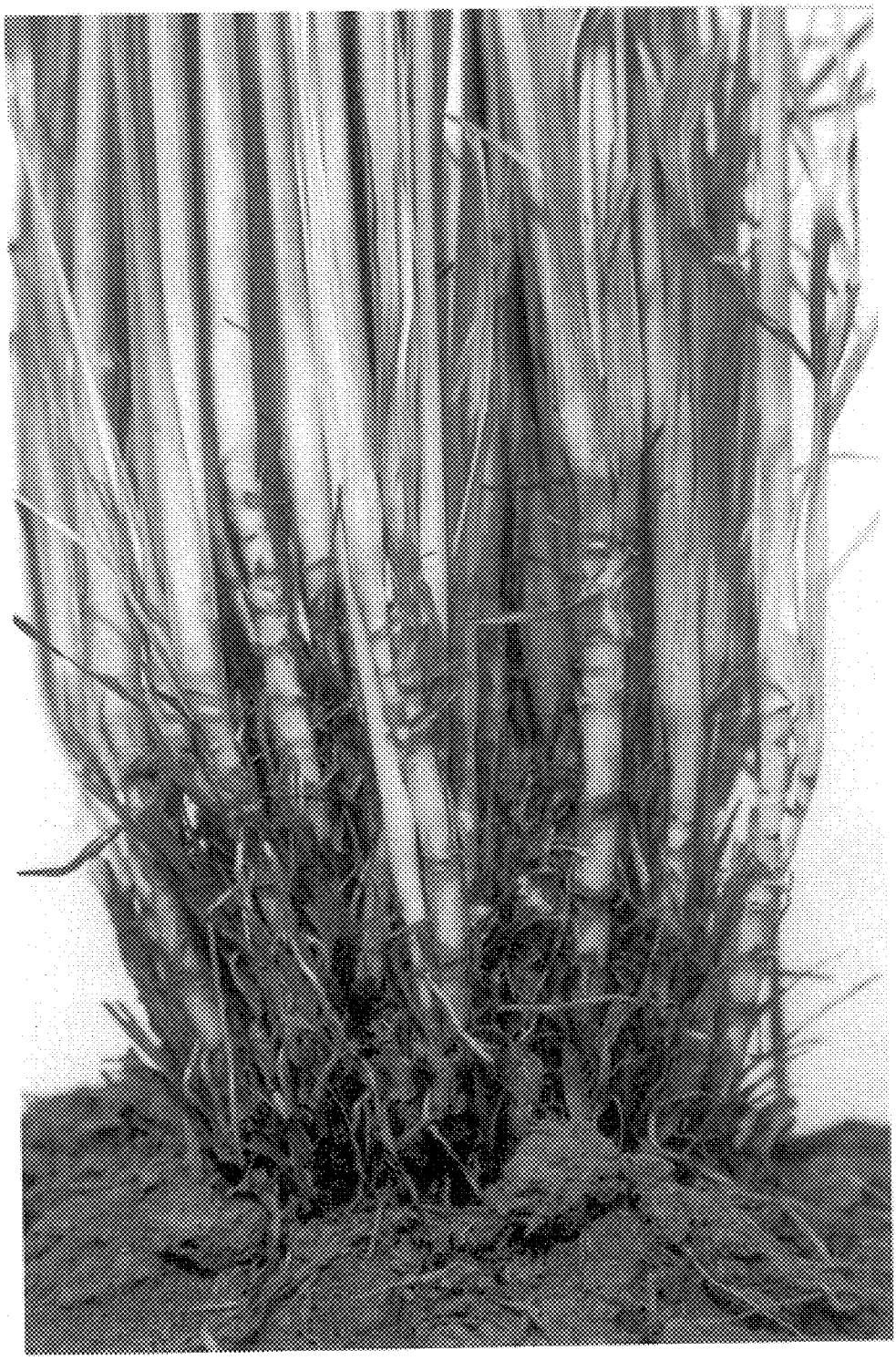
FIG. 4. A 'Jal Pallavi' plant (3 years old) exhibiting the 'Marker' character for water logging tolerance: Stem elongation at the plant base and leaf sheath.
Figure 5:
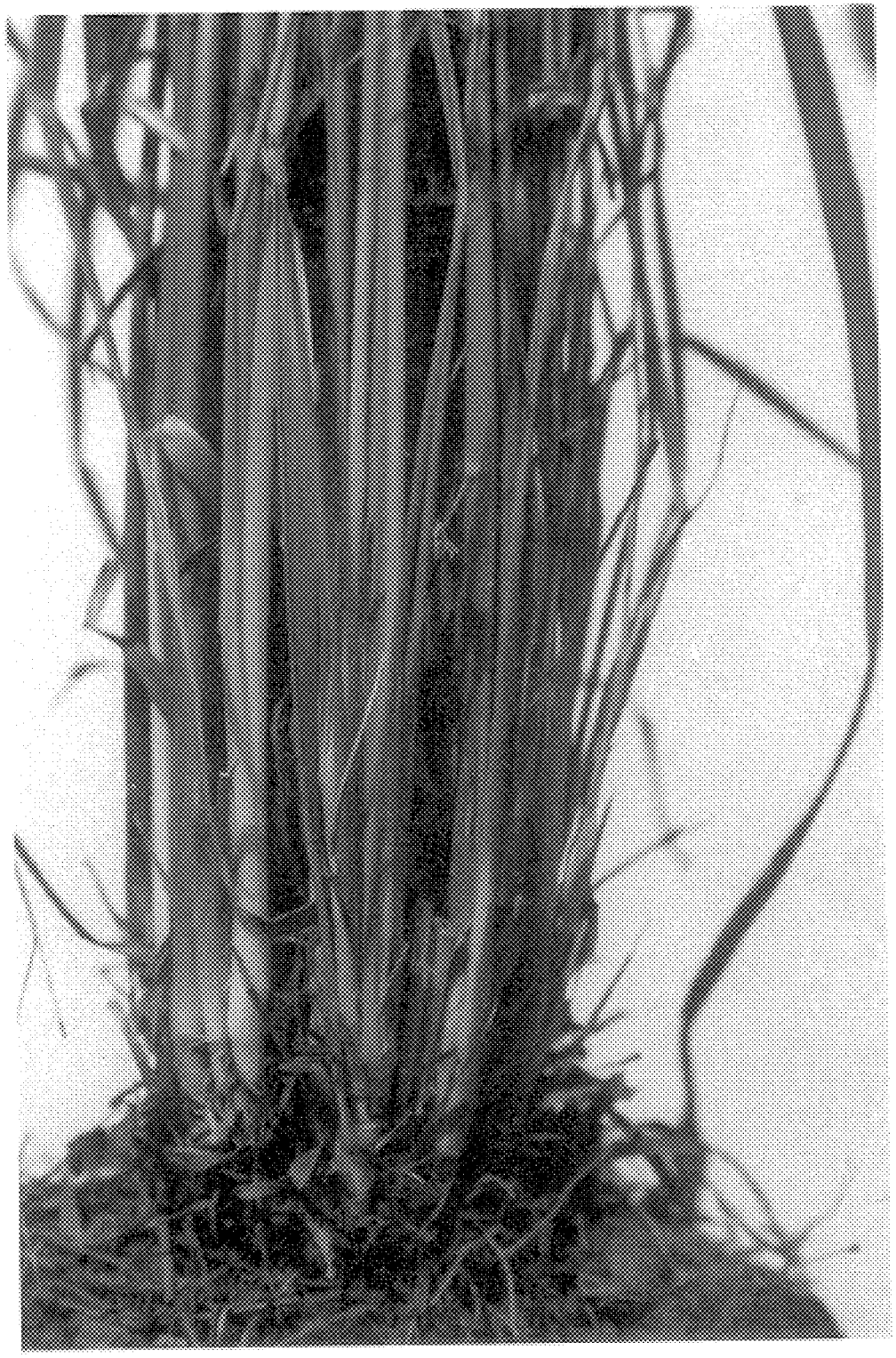
FIG. 5. A plant of normal variety showing no stem elongation between plant base and leaf sheath.

1. Mature growth habit in width: The space-planted 'Jal Pallavi' plants (with wider plant spacing of 1.5 m×1.5 m against the normal plant spacing of 60 cm×30 cm) (FIG. 1) measure 1.3 m–1.4 m in width against 1.0–1.3, of the plants of normal varieties, when both classes of plants are quite a mature (2 years old). 'Jal Pallavi' has culms having a solid stem unusually elongated between the plant base and leaf sheath. Such stem elongation is the major morphological 'marker' to identify the water logging tolerance of the plant (FIG. 3 and 4).
2. Leaf blade shape: Linear lanceolate.
3. Leaf blade apex shape: Acuminate.
4. Leaf blade margin: Entire.
5. Surface texture of leaf blade (both lower and upper side): Thick with minute hairs on the upper surface; Lower surface glabrous.
6. Leaf blade fragrance: Pleasant aroma (due to major essential oil constituents; critonellol, citronellal and gerniol) comes out when leaf blade is rubbed between fingers.
7. Leaf blade colour designation (both upper and lower side) on on R.H.S. colour Chart: Upper side yellow green with the colour code 146B on R.H.S. colour chart; lower side yellow green with the colour code 147B (FIG. 2) the R.H.S. colour chart as against green (137A) at the upper surface and green (137B) at the lower surface of the others.
8. Leaf sheath length: 35–40 cm.
9. Leaf sheath type: Tubular (Open tube surrounding the stem) (FIG. 3).
10. Leaf sheath colour designation — on R.H.S. colour chart: Red purple with the colour code 70B on R.H.S. colour chart (FIG. 3).
11. Leaf sheath margin: Membranous and entire.
12. Leaf sheath surface texture: Glabrous.
13. Culms size: Each circular (terete) culm measuring 40–46 cm for length and 2.2–2.6 cm in width.
14. Culms colour designation — on R.H.S. colour chart: Yellowish green with colour code 147D on R.H.S. colour chart.
15. Culms surface texture: Smooth and glossy.
16. Ligules size: Small in size 0.3 cm in length (along the stem girth) and 0.1 cm in width (along the stem length), occurring in pairs at the junction of leaf blade and leaf sheath.
17. Ligules colour designation — on The R.H.S. colour chart: Orange red with the colour code 31C on The R.H.S. colour chart.
18. Ligules surface texture: Smooth and membranous.
19. Ligules shape: Truncate.
20. Inflorescence size: Inflorescence 45–56 cm long and 30–33 cm wide.
21. Inflorescence arrangement: Inflorescence (loose panicle) comprising plural branches, each of which is supported by a spahathe; the ultimate unit of spathate panicle consists of a pair of racemes, each is supported by a stalk called a raceme-base. The bases are fused together above the point where they are articulated with the common peduncle; each raceme measuring 16–19 mm in length, is often deflexed and consists of several pairs of spikelets. In each spikelet pair one spikelet is sessile and the other pedicelled. The sessile spikelet is hermaphrodite and the pedicelled spikelet is male.
22. Inflorescence colour designation — on R.H.S. colour chart: Yellow green (144B) (in beginning) to orange red (31B) (at the later phase).
23. Root type: Fibrous.
24. Pest resistance: Resistant to pests, as axiomatic to the marked absence of the earlier reported common pests especially shoot borer (*Chilo infuscatellus,* Thrips (*Anaphothrips sundanensis*), Aphid (*Macrosiphum miscanthi*), Leafhopper (*Ziginia macensis*) and mites (*Eriophyces cymbopogon*).
25. Seed colour: Greyed purple (187D).
26. Seed shape: Trigone.
27. Seed size: Shrivelled seeds measuring 0.4 mm×0.2 mm in size.
28. Seed surface texture: Wrinkled with minute hairs at the tip.
29. Stem shape: Terete.
30. Stem habit: Bold and solid stem against soft stem (culm) of the others; Stem showing unusual elongation between plant base and leaf sheath. Such growth habit of stem, as mentioned earlier, is the major morphological 'marker' for the prognosis of water logging tolerance of 'Jal Pallavi'.
31. Number of nodes:
    *I. Primary nodes.*—15–20.
    *II. Secondary nodes.*—12–16.
    *III. Tertiary note.*—It does not occur.
32. Average length of primary internodes: 15–20 mm.
33. Leaf lamina base shape: Circular (open and amplexixaul (i.e. surrounding the stem).
34. Peteole shape: It is not peteole but leaf sheath (described earlier).
35. Number of trichomes: Trichomes do not occur (Glandular Trichomes occur in some diocotyledonous aromatic plant like Mentha but not in monocots).
36. Time of flowering: During spring (March–April) and Autumn (September–October).
37. Lastingness as bloom: For each flower 10–12 hrs (but span of flowering of the plants is 10–12 days).
38. Flower shape: Cup shape largely given by the four glumes, (flowering glume, lemma and its associated gluma palea and the basal two emply glumes), which enclose the flower (most of the time the flower does not open but invariably pushes out the feathery stigma before anthesis to facilitate its out-crossing).
39. Pedicel length: Grooved pedicel measures 1–2 mm in length (pedicel occurs only in the male spikelets).
40. Calyx diameter: The plant does not have dalyx but the emply glumes which contain the flower.
41. Calyx colour designation: Not applicable.
42. Corolla: Two petals are modified into perianths, called as lodicules.
43. Corolla colour — on R.H.S. colour chart: Modified petals (lodicules) faint green (it does not match The R.H.S. colour chart).
44. Pubescence of corolla: Non pubescent.
45. Number of anthers: Three (versatile anthers).
46. Anther colour designation — on R.H.S. colour: Green (147D).
47. Stigma: Feathery stigma.
48. Ovaries: Superior, one celled with one ovule.
49. Colour of stigma: Reddish purple (70A).
50. Colour of ovaries: Green (147D).

Details of Cloning of the Plant

The water logging tolerant plant 'Jal Pallavi' was vegetatively cloned at the field station of Central Institute of Medicinal and Aromatic Plants (CIMAP) which is at Pantnagar, Uttar Pradesh, India. As to the character of the area (Pantnagar) where the plant (Jal Pallavi) has been vegetatively cloned from the original genotype WTC-1 (Water Tolerant Citronella), is situated at the sub-tropical foot hill belt, a major aromatic crop growing area of India. The soil of the experimental site at Pantnagar was clay-loamy in texture, high in organic carbon (1.16%), medium in available P (180.0 kg/ha) and K (200.0 kg/ha) with normal pH (7.0). The being located at a latitude of 29 N., longitude of 79.30 E. and at an altitude of 244M above mean see level, it gets the minimum temperature ranging between 3–8° C. and maximum temperature ranging between 17 and 25° C. during winter months. The corresponding ranges for the minimum and maximum temperature, which the crop usually receives during its growth period in spring and summer are 9 to 25° C. and 25 to 42° C., respectively. The total rainfull over the area in different months of the years during 1994 to 1999 ranged between 1.2 mm (during winter) to 336.0 mm (during rains).

The original plant WTC-1 (Jal Pallavi) as well as the rest 4999 normal Jorlab-2 plants (sister plants of Jal Pallavi, that had no water logging tolerance) were maintained in the aquatic experimental field for the whole year (January 1994 to December 1995) (size of the field: 850 sq. m. And plant spacing: 60 cm×30 cm). During September, 1994 when the plant WTC-1 appeared as a full grown individual with as high as 60 tillers, a total of 50 tillers were drawn from WTC-1 and transplanted in a separate bed as its second vegetative generation (VG2)=leaving the rest part of its clump comprising 10 tillers as original plant (VG1) in the aquatic experimental field. During February, 1995 all the VG 2 plants having the morphological plant attributes identical with that of the original plant (WTC-1), were uprooted and their tillers (Average tillers/plant: 40) were planted in field plots allotted to the preliminary yield trial (PYT) as well as the plots allotted to the vegetative multiplication of Jal Pallavi. The PYT was conducted in the fashion of a Randomized Block Design with six treatments (varieties: Jal Pallavi+five control cultivars: Bio-13, Manjusha, Mandakini, Jorlab-2 (the mother variety) and Pantnagar Local) and three replications for each treatment. The plot size in PYT measured 10 m×3 m for each treatment and was sufficient to accommodate a total of 166 plants spaced at 60 cm×30 cm plant spacing. The proportion of the VG2 tillers of Jal Pallavi, Planted in PYT and the vegetative multiplication block (VMB) with the similar plant spacing (60 cm×30 cm) was: PTY:VMB:500:1500. The plants of both PYT and VMB were maintained with the normal cultural practices. The first harvest data in PYT with VG2 plants was collected during June, 1995 and the second harvest data during October, 1995. The VG2 plants in VMB attained full growth by having 60 tillers per plant during February 1996. Of the total of 90,000 tillers drawn from the 1500 VG2 plants of VMB, 1200 were used in conducting the pitol scale yield trial (PST) and the rest 88,800 were planted in bigger VMB (1.6 ha) and grown as VG3 generation. The PST was conducted during 1996–1999 in the fashion of RBD with 6 treatments (including Jal Pallavi) and 3 replications. The plot size in PST measured 16 m×5 m and could accomodate 400 plants with 60 cm×30 cm plant spacing.

To abridge, Jal Pallavi was vegetatively reproduced (clones) two times (for raising VG2 and VG3 generation) from the original plant (WTC-1) comprising 60 tillers (VG1 generation) and every time the reproduced stock was morphophysiologically identical with the original plant (WTC-1).

Randomly Amplified Polymorphic DNA Analysis

Type of analysis used by the applicant to determine the genetic distance using RAPD marker.

In order to study at the molecular level the diversity and genetic relationships among the plant Jal Pallavi and mother five cultivars: Bio-13, Manjusha, Jorlab-2 (the mother cultivar), Manjusha, Ceylon citronella and Mandakini, twenty arbitrary primers (Table 7 in the earlier submitted original version for the invention) were used for RAPD analysis of their isolated DNA. The DNA was isolated from 40 mg of leaf tissue essentially according to the protocol of Doyle and Doyle (1987). Polymerase chain reactions (PCRs) were carried out in 25 $\mu$L volume A reaction tube contained 25 mg of DNA, 0.2 unit of Taq DNA polymerase, 100 $\mu$M each of dNTPs, 1.5 mM $MgCi_2$ and 5 p mol of decanucleotide primers. The amplifications were carried out using the DNA Engine thermal Cycler (MJ Research, USA following the protocol described earlier (Shasany et al. 1998). The amplified products were loaded in 1.2% agarose gel containing 0.5 $\mu$G ml- of ethidium bromide and photographed by polaroid system. Custom-made decanucleotide primers (M A P 0 1 to M A P 2 0) were used for the analysis.

The similarity among the cultivars for specific DNA band(s) were measured by the help of the similarity matrix obtained after multivariate analysis using Nei and Li's coefficient (Nei and Li, 1979), of the distance index (1-similarity index between the genotypes) were found out to measure the diversity between the cultivars.

The RAPD patterns of the plants are completely different from those of the parent ('Jorlab-2') as well as of the known released varieties 'Manjusha', 'Mandakini', 'Bio-13' and Ceylon. The plant of the present invention was being developed by planned selection and thus is distinct, unique, novel and can be used for various medicinal and aromatic purposes. The plant has better morphological and economical traits and is available only with us in CIMAP. No variation in the RAPD patterns were observed in the DNA analysis of the population for three generations indicating the stability of the genotype. The following primers (Table 7) were used to calculate the similarity of 'Jal Pallavi' with the control (Table 8).

TABLE 7

| Primers | | Nucleotide Sequence |
|---|---|---|
| 1. | MAP 01 SEQ ID NO:1 | 5' AAA TCG GAG C 3' |
| 2. | MAP 02 SEQ ID NO:2 | 5' GTC CTA CTC G 3' |
| 3. | MAP 03 SEQ ID NO:3 | 5' GTC CTT AGC G 3' |
| 4. | MAP 04 SEQ ID NO:4 | 5' TGC GCG ATC G 3' |
| 5. | MAP 05 SEQ ID NO:5 | 5' AAC GTA CGC G 3' |
| 6. | MAP 06 SEQ ID NO:6 | 5' GCA CGC CGG A 3' |
| 7. | MAP 07 SEQ ID NO:7 | 5' CAC CCT GCG C 3' |
| 8. | MAP 08 SEQ ID NO:8 | 5' CTA TCG CCG C 3' |
| 9. | MAP 09 SEQ ID NO:9 | 5' CGG GAT CCG C 3' |
| 10 | MAP 10 SEQ ID NO:10 | 5' GCG AAT TCC G 3' |
| 11. | MAP 11 SEQ ID NO:11 | 5' CCC TGC AGG C 3' |
| 12 | MAP 12 SEQ ID NO:12 | 5' CCA AGC TTG C 3' |
| 13 | MAP 13 SEQ ID NO:13 | 5' GTG CAA TGA G 3' |
| 14 | MAP 14 SEQ ID NO:14 | 5' AGG ATA CGT G 3' |
| 15 | MAP 15 SEQ ID NO:15 | 5' AAG ATA GCG G 3' |
| 16 | MAP 16 SEQ ID NO:16 | 5' GGA TCT GAA C 3' |
| 17 | MAP 17 SEQ ID NO:17 | 5' TTG TCT CAG G 3' |
| 18 | MAP 18 SEQ ID NO:18 | 5' CAT CCC GAA C 3' |
| 19 | MAP 19 SEQ ID NO:19 | 5' GGA CTC CAC G 3' |
| 20 | MAP 20 SEQ ID NO:20 | 5' AGC CTG ACG C 3' |

(MAP-Medicinal and Aromatic Plants)

TABLE 8

Similarities and distances of 'Jal Pallavi' with other released varieties of citronella based on RAPD analysis

| | Bio-13 | Jal Pallavi | Jorlab-2 | Manjusha | Ceylon | Mandakini |
|---|---|---|---|---|---|---|
| Bio-13 | 1.000 (0) | | | | | |
| Jal Pallavi | 0.349 (0.651) | 1000 (0) | | | | |
| Jorlab-2 | 0.330 (0.670) | 0.797 (0.203) | 1.000 (0) | | | |
| Manjusha | 0.316 (0.684) | 0.444 (0.556) | 0.549 (0.451) | 1.000 (0) | | |
| Ceylon | 0.372 (0.628) | 0.327 (0.673) | 0.328 (0.672) | 0.360 (0.640) | 1.000 (0) | |
| Mandakini | 0.425 (0.575) | 0.391 (0.609) | 0.391 (0.609) | 0.440 (0.560) | 0.314 (0.589 | 1.000 (0) |

Following primers purchased from Operon Technologies (HAS) were used to develop the unique RAPD profiles of the plant 'Jal Pallavi' (Table 9 and Photograph #5)

TABLE 9

| Primers | Nucleotide sequence |
|---|---|
| 1. OPT 01 SEQ ID NO:21 | 5' GGG CCA CTC A 3' |
| 2. OPT 02 SEQ ID NO:22 | 5' GGA GAG ACT C 3' |
| 3. OPT 03 SEQ ID NO:23 | 5' TCC ACT CCT G 3' |
| 4. OPT 04 SEQ ID NO:24 | 5' CAC AGA GGG A 3' |
| 5. OPT 05 SEQ ID NO:25 | 5' GGG TTT GGC A 3' |
| 6. OPT 06 SEQ ID NO:26 | 5' CAA GGG CAG A 3' |
| 7. OPT 07 SEQ ID NO:27 | 5' GGC AGG CTG T 3' |
| 8. OPT 08 SEQ ID NO:28 | 5' AAC GGC GAC A 3' |
| 9. OPT 09 SEQ ID NO:29 | 5' CAC CCC TGA G 3' |
| 10. OPT 10 SEQ ID NO:30 | 5' TTC CCC GCG A 3' |
| 11. OPT 11 SEQ ID NO:31 | 5' GGG TGT GTA G 3' |
| 12. OPT 12 SEQ ID NO:32 | 5' AAT GCC GCA G 3' |
| 13. OPT 13 SEQ ID NO:33 | 5' GGA TGC CAC T 3' |
| 14. OPT 14 SEQ ID NO:34 | 5' GGT GAA CGC T 3' |
| 15. OPT 15 SEQ ID NO:35 | 5' CCA ACG TCG T 3' |
| 16. OPT 16 SEQ ID NO:36 | 5' GAT GCC AGA C 3' |
| 17. OPT 17 SEQ ID NO:37 | 5' GTC CGT ATG G 3' |
| 18. OPT 18 SEQ ID NO:38 | 5' GAC CAA TGC C 3' |

Disease Resistance

Information relating to plant disease/Insect-pest resistance/susceptibility is as follows.

Attempts were made during 1995–98 to regularly examine the field grown plants of Jal Pallavi and the five control varieties (Bio-13, Jorlab-2, Manjusha, Mandakini). All the six varieties, with rare exception in Pantnagar Local which showed very negligible infestation (0.8%) of the sucking stem borer (*Chilo Infascatsllus*), did not exhibit any infestation of insect-pest.

Studies on disease resistance were conducted prior to each of the 4 consecutive harvests (cuts) of the crop after planting and the reaction of the new variety 'Jal Pallavi' as well as five control varieties: 'Bio-13', 'Manjusha', 'Mandakini', 'Jorlab-2', and 'Pantnagar Local' to the earlier reported diseases: leaf blight caused by *Curvularia andropogonis* (Alam and Husain, 1976; Alam, et al. 1983) and *Drechlera autraliensis* (Ramiah and Chandrashekhar, 1981), purple leaf spot caused by *Colletotrichum graminicola* (Sarwar et al., 1980), lethal yellowing caused by *Pythium aphanidermatum* (Alam et al., 1992), colar rot and wilt caused by *Fusarium moniliforme* (Alam et al., 1994) and sheath and leaf blight caused by *Rhizoctonia solani* (Singh et al., 1997) were recorded sheath and leaf blight and purple leaf spot scored on modified 9-point disease scale, where 1=0%, 2=1 to 5%, 3=6 to 10%, 4=11 to 20%, 5=21 to 30% 6=31 to 40%, 7=41 to 60%, 8=61 to 80% and 9=81 to 100% foliage destroyed. Any variety with 1 to 3% score in the scale was considered resistant. As to the scoring in respect to lethal yellowing (LY), colar rot (CR) and wilt (W) diseases reactions were found out on the basis of percent infected plants. Table 10 shows the results convincingly indicating the relative resistance of the new variety 'Jal Pallavi'. During the whole experimental period till date, 'Jal Pallavi' as well as all the control genotypes have not revealed any infestation of insect pests.

Information on Cold and Drough Tolerance

The water requirements of the new variety Jal Pallavi as well as all the existing standard varieties are very high and invariably they are susceptible to drought and water stress. Likewise, Jal Pallavi as well as the other citronella genotypes do not have much tolerance to cold and frosting, as it had been aromatic to their poor growth and biomass production during hard winter.

SEQUENCE LISTING

```
<160> NUMBER OF SEQ ID NOS:   38

<210> SEQ ID NO 1
<211> LENGTH: 10
<212> TYPE: DNA
<213> ORGANISM: Artificial
<220> FEATURE:
<223> OTHER INFORMATION: MAP 01 Primer - Primer used in RAPD analysis
      comparing Jal Pallavi with Jorlab-2, Manjusha, Mandakini, Bio-13,
      and Ceylon.

<400> SEQUENCE: 1

aaatcggagc                                                          10


<210> SEQ ID NO 2
```

-continued

<211> LENGTH: 10
<212> TYPE: DNA
<213> ORGANISM: Artificial
<220> FEATURE:
<223> OTHER INFORMATION: MAP 02 Primer - Primer used in RAPD analysis
comparing Jal Pallavi with Jorlab-2, Manjusha, Mandakini, Bio-13,
and Ceylon.

<400> SEQUENCE: 2 gtcctactcg 10

<210> SEQ ID NO 3
<211> LENGTH: 10
<212> TYPE: DNA
<213> ORGANISM: Artificial
<220> FEATURE:
<223> OTHER INFORMATION: MAP 03 Primer - Primer used in RAPD analysis
comparing Jal Pallavi with Jorlab-2, Manjusha, Mandakini, Bio-13,
and Ceylon.

<400> SEQUENCE: 3 gtccttagcg 10

<210> SEQ ID NO 4
<211> LENGTH: 10
<212> TYPE: DNA
<213> ORGANISM: Artificial
<220> FEATURE:
<223> OTHER INFORMATION: MAP 04 Primer - Primer used in RAPD analysis
comparing Jal Pallavi with Jorlab-2, Manjusha, Mandakini, Bio-13,
and Ceylon.

<400> SEQUENCE: 4 tgcgcgatcg 10

<210> SEQ ID NO 5
<211> LENGTH: 10
<212> TYPE: DNA
<213> ORGANISM: Artificial
<220> FEATURE:
<223> OTHER INFORMATION: MAP 05 Primer - Primer used in RAPD analysis
comparing Jal Pallavi with Jorlab-2, Manjusha, Mandakini, Bio-13,
and Ceylon.

<400> SEQUENCE: 5 aacgtacgcg 10

<210> SEQ ID NO 6
<211> LENGTH: 10
<212> TYPE: DNA
<213> ORGANISM: Artificial
<220> FEATURE:
<223> OTHER INFORMATION: MAP 06 Primer - Primer used in RAPD analysis
comparing Jal Pallavi with Jorlab-2, Manjusha, Mandakini, Bio-13,
and Ceylon.

<400> SEQUENCE: 6 gcacgccgga 10

<210> SEQ ID NO 7
<211> LENGTH: 10
<212> TYPE: DNA
<213> ORGANISM: Artificial
<220> FEATURE:
<223> OTHER INFORMATION: MAP 07 Primer - Primer used in RAPD analysis
comparing Jal Pallavi with Jorlab-2, Manjusha, Mandakini, Bio-13,
and Ceylon.

-continued

<400> SEQUENCE: 7 caccctgcgc 10

<210> SEQ ID NO 8
<211> LENGTH: 10
<212> TYPE: DNA
<213> ORGANISM: Artificial
<220> FEATURE:
<223> OTHER INFORMATION: MAP 08 Primer - Primer used in RAPD analysis comparing Jal Pallavi with Jorlab-2, Manjusha, Mandakini, Bio-13, and Ceylon.

<400> SEQUENCE: 8 ctatcgccgc 10

<210> SEQ ID NO 9
<211> LENGTH: 10
<212> TYPE: DNA
<213> ORGANISM: Artificial
<220> FEATURE:
<223> OTHER INFORMATION: MAP 09 Primer - Primer used in RAPD analysis comparing Jal Pallavi with Jorlab-2, Manjusha, Mandakini, Bio-13, and Ceylon.

<400> SEQUENCE: 9 cgggatccgc 10

<210> SEQ ID NO 10
<211> LENGTH: 10
<212> TYPE: DNA
<213> ORGANISM: Artificial
<220> FEATURE:
<223> OTHER INFORMATION: MAP 10 Primer - Primer used in RAPD analysis comparing Jal Pallavi with Jorlab-2, Manjusha, Mandakini, Bio-13, and Ceylon.

<400> SEQUENCE: 10 gcgaattccg 10

<210> SEQ ID NO 11
<211> LENGTH: 10
<212> TYPE: DNA
<213> ORGANISM: Artificial
<220> FEATURE:
<223> OTHER INFORMATION: MAP 11 Primer - Primer used in RAPD analysis comparing Jal Pallavi with Jorlab-2, Manjusha, Mandakini, Bio-13, and Ceylon.

<400> SEQUENCE: 11 ccctgcaggc 10

<210> SEQ ID NO 12
<211> LENGTH: 10
<212> TYPE: DNA
<213> ORGANISM: Artificial
<220> FEATURE:
<223> OTHER INFORMATION: MAP 12 Primer - Primer used in RAPD analysis comparing Jal Pallavi with Jorlab-2, Manjusha, Mandakini, Bio-13, and Ceylon.

<400> SEQUENCE: 12 ccaagcttgc 10

<210> SEQ ID NO 13
<211> LENGTH: 10
<212> TYPE: DNA

-continued

<213> ORGANISM: Artificial
<220> FEATURE:
<223> OTHER INFORMATION: MAP 13 Primer - Primer used in RAPD analysis
comparing Jal Pallavi with Jorlab-2, Manjusha, Mandakini, Bio-13,
and Ceylon.

<400> SEQUENCE: 13 gtgcaatgag 10

<210> SEQ ID NO 14
<211> LENGTH: 10
<212> TYPE: DNA
<213> ORGANISM: Artificial
<220> FEATURE:
<223> OTHER INFORMATION: MAP 14 Primer - Primer used in RAPD analysis
comparing Jal Pallavi with Jorlab-2, Manjusha, Mandakini, Bio-13,
and Ceylon.

<400> SEQUENCE: 14 aggatacgtg 10

<210> SEQ ID NO 15
<211> LENGTH: 10
<212> TYPE: DNA
<213> ORGANISM: Artificial
<220> FEATURE:
<223> OTHER INFORMATION: MAP 15 Primer - Primer used in RAPD analysis
comparing Jal Pallavi with Jorlab-2, Manjusha, Mandakini, Bio-13,
and Ceylon.

<400> SEQUENCE: 15 aagatagcgg 10

<210> SEQ ID NO 16
<211> LENGTH: 10
<212> TYPE: DNA
<213> ORGANISM: Artificial
<220> FEATURE:
<223> OTHER INFORMATION: MAP 16 Primer - Primer used in RAPD analysis
comparing Jal Pallavi with Jorlab-2, Manjusha, Mandakini, Bio-13,
and Ceylon.

<400> SEQUENCE: 16 ggatctgaac 10

<210> SEQ ID NO 17
<211> LENGTH: 10
<212> TYPE: DNA
<213> ORGANISM: Artificial
<220> FEATURE:
<223> OTHER INFORMATION: MAP 17 Primer - Primer used in RAPD analysis
comparing Jal Pallavi with Jorlab-2, Manjusha, Mandakini, Bio-13,
and Ceylon.

<400> SEQUENCE: 17 ttgtctcagg 10

<210> SEQ ID NO 18
<211> LENGTH: 10
<212> TYPE: DNA
<213> ORGANISM: Artificial
<220> FEATURE:
<223> OTHER INFORMATION: MAP 18 Primer - Primer used in RAPD analysis
comparing Jal Pallavi with Jorlab-2, Manjusha, Mandakini, Bio-13,
and Ceylon.

<400> SEQUENCE: 18

-continued catcccgaac 10

<210> SEQ ID NO 19
<211> LENGTH: 10
<212> TYPE: DNA
<213> ORGANISM: Artificial
<220> FEATURE:
<223> OTHER INFORMATION: MAP 19 Primer - Primer used in RAPD analysis comparing Jal Pallavi with Jorlab-2, Manjusha, Mandakini, Bio-13, and Ceylon.

<400> SEQUENCE: 19 ggactccacg 10

<210> SEQ ID NO 20
<211> LENGTH: 10
<212> TYPE: DNA
<213> ORGANISM: Artificial
<220> FEATURE:
<223> OTHER INFORMATION: MAP 20 Primer - Primer used in RAPD analysis comparing Jal Pallavi with Jorlab-2, Manjusha, Mandakini, Bio-13, and Ceylon.

<400> SEQUENCE: 20 agcctgacgc 10

<210> SEQ ID NO 21
<211> LENGTH: 10
<212> TYPE: DNA
<213> ORGANISM: Artificial
<220> FEATURE:
<223> OTHER INFORMATION: OPT 01 Primer - Used to develop the unique RAPD profiles of the plant Jal Pallavi

<400> SEQUENCE: 21 gggccactca 10

<210> SEQ ID NO 22
<211> LENGTH: 10
<212> TYPE: DNA
<213> ORGANISM: Artificial
<220> FEATURE:
<223> OTHER INFORMATION: OPT 02 Primer - Used to develop the unique RAPD profiles of the plant Jal Pallavi

<400> SEQUENCE: 22 ggagagactc 10

<210> SEQ ID NO 23
<211> LENGTH: 10
<212> TYPE: DNA
<213> ORGANISM: Artificial
<220> FEATURE:
<223> OTHER INFORMATION: OPT 03 Primer - Used to develop the unique RAPD profiles of the plant Jal Pallavi

<400> SEQUENCE: 23 tccactcctg 10

<210> SEQ ID NO 24
<211> LENGTH: 10
<212> TYPE: DNA
<213> ORGANISM: Artificial
<220> FEATURE:
<223> OTHER INFORMATION: OPT 04 Primer - Used to develop the unique RAPD profiles of the plant Jal Pallavi -continued

<400> SEQUENCE: 24 cacagaggga 10

<210> SEQ ID NO 25
<211> LENGTH: 10
<212> TYPE: DNA
<213> ORGANISM: Artificial
<220> FEATURE:
<223> OTHER INFORMATION: OPT 05 Primer - Used to develop the unique RAPD
profiles of the plant Jal Pallavi

<400> SEQUENCE: 25 gggtttggca 10

<210> SEQ ID NO 26
<211> LENGTH: 10
<212> TYPE: DNA
<213> ORGANISM: Artificial
<220> FEATURE:
<223> OTHER INFORMATION: OPT 06 Primer - Used to develop the unique RAPD
profiles of the plant Jal Pallavi

<400> SEQUENCE: 26 caagggcaga 10

<210> SEQ ID NO 27
<211> LENGTH: 10
<212> TYPE: DNA
<213> ORGANISM: Artificial
<220> FEATURE:
<223> OTHER INFORMATION: OPT 07 Primer - Used to develop the unique RAPD
profiles of the plant Jal Pallavi

<400> SEQUENCE: 27 ggcaggctgt 10

<210> SEQ ID NO 28
<211> LENGTH: 10
<212> TYPE: DNA
<213> ORGANISM: Artificial
<220> FEATURE:
<223> OTHER INFORMATION: OPT 08 Primer - Used to develop the unique RAPD
profiles of the plant Jal Pallavi

<400> SEQUENCE: 28 aacggcgaca 10

<210> SEQ ID NO 29
<211> LENGTH: 10
<212> TYPE: DNA
<213> ORGANISM: Artificial
<220> FEATURE:
<223> OTHER INFORMATION: OPT 09 Primer - Used to develop the unique RAPD
profiles of the plant Jal Pallavi

<400> SEQUENCE: 29 caccccctgag 10

<210> SEQ ID NO 30
<211> LENGTH: 10
<212> TYPE: DNA
<213> ORGANISM: Artificial
<220> FEATURE:
<223> OTHER INFORMATION: OPT 11 Primer - Used to develop the unique RAPD
profiles of the plant Jal Pallavi -continued

<400> SEQUENCE: 30 ttccccgcga 10

<210> SEQ ID NO 31
<211> LENGTH: 10
<212> TYPE: DNA
<213> ORGANISM: Artificial
<220> FEATURE:
<223> OTHER INFORMATION: OPT 12 Primer - Used to develop the unique RAPD
profiles of the plant Jal Pallavi

<400> SEQUENCE: 31 gggtgtgtag 10

<210> SEQ ID NO 32
<211> LENGTH: 10
<212> TYPE: DNA
<213> ORGANISM: Artificial
<220> FEATURE:
<223> OTHER INFORMATION: OPT 14 Primer - Used to develop the unique RAPD
profiles of the plant Jal Pallavi

<400> SEQUENCE: 32 aatgccgcag 10

<210> SEQ ID NO 33
<211> LENGTH: 10
<212> TYPE: DNA
<213> ORGANISM: Artificial
<220> FEATURE:
<223> OTHER INFORMATION: OPT 15 Primer - Used to develop the unique RAPD
profiles of the plant Jal Pallavi

<400> SEQUENCE: 33 ggatgccact 10

<210> SEQ ID NO 34
<211> LENGTH: 10
<212> TYPE: DNA
<213> ORGANISM: Artificial
<220> FEATURE:
<223> OTHER INFORMATION: OPT 16 Primer - Used to develop the unique RAPD
profiles of the plant Jal Pallavi

<400> SEQUENCE: 34 ggtgaacgct 10

<210> SEQ ID NO 35
<211> LENGTH: 10
<212> TYPE: DNA
<213> ORGANISM: Artificial
<220> FEATURE:
<223> OTHER INFORMATION: OPT 17 Primer - Used to develop the unique RAPD
profiles of the plant Jal Pallavi

<400> SEQUENCE: 35 ccaacgtcgt 10

<210> SEQ ID NO 36
<211> LENGTH: 10
<212> TYPE: DNA
<213> ORGANISM: Artificial
<220> FEATURE:
<223> OTHER INFORMATION: OPT 18 Primer - Used to develop the unique RAPD
profiles of the plant Jal Pallavi -continued

```
<400> SEQUENCE: 36

gatgccagac                                                          10


<210> SEQ ID NO 37
<211> LENGTH: 10
<212> TYPE: DNA
<213> ORGANISM: Artificial
<220> FEATURE:
<223> OTHER INFORMATION: OPT 19 Primer - Used to develop the unique RAPD
      profiles of the plant Jal Pallavi

<400> SEQUENCE: 37

gtccgtatgg                                                          10


<210> SEQ ID NO 38
<211> LENGTH: 10
<212> TYPE: DNA
<213> ORGANISM: Artificial
<220> FEATURE:
<223> OTHER INFORMATION: OPT 20 Primer - Used to develop the unique RAPD
      profiles of the plant Jal Pallavi

<400> SEQUENCE: 38

gaccaatgcc                                                          10
```

We claim:

1. A novel, distinct, high yielding and stable variety of citronella plant *Cymbopogon winterianus,* named 'Jal Pallavi' characterized by the combination of characteristics:

(a) highly adapted to both favorable as well as unfavorable environments of continuous and aberrant water stagnation situations, (b) production of more biomass (herbage yield) in comparison to the existing citronella varieties, (c) production of essential oil with pleasant smell conforming to the standard concentrations for the major oil components citronellal, citronellol, and geraniol much useful in pharmaceutical/aromatic preparations for various applications, (d) unique RAPD profile, compared to those of the existing citronella varieties, (e) exhibiting least reduction in yield (herbage as well as essential oil) over years and thus constitutes the most suitable material for perennial plantations, (f) substantially high oil yield, at least 1.22%, with the following oil constituents to a maximum extent of citronellal at least 40.7%, citronellol at least 10.7%, geraniol at least 17.5% and the rest being unidentified fractions in the essential oil, all totaling to 100% at different stages of growth, substantially as shown and described.

* * * * *